US011010716B2

(12) United States Patent
Thesman

(10) Patent No.: US 11,010,716 B2
(45) Date of Patent: May 18, 2021

(54) HEALTH PLAN RATING SYSTEM IMPROVEMENT PROGRAM

(71) Applicant: Debra Thesman, Rocklin, CA (US)

(72) Inventor: Debra Thesman, Rocklin, CA (US)

(73) Assignee: STAR MEASURES INVESTMENTS, LLC, Carson City, NV (US)

( * ) Notice: Subject to any disclaimer, the term of this patent is extended or adjusted under 35 U.S.C. 154(b) by 0 days.

(21) Appl. No.: 14/227,245

(22) Filed: Mar. 27, 2014

(65) Prior Publication Data

US 2014/0214444 A1 Jul. 31, 2014

Related U.S. Application Data

(63) Continuation of application No. 13/294,381, filed on Nov. 11, 2011, now abandoned.

(51) Int. Cl.
*G06Q 50/22* (2018.01)
*G06Q 10/10* (2012.01)
*G16H 10/60* (2018.01)
*G16H 20/10* (2018.01)

(52) U.S. Cl.
CPC ............ *G06Q 10/10* (2013.01); *G16H 10/60* (2018.01); *G16H 20/10* (2018.01)

(58) Field of Classification Search
USPC ........................ 705/2-4, 7.38-7.41
See application file for complete search history.

(56) References Cited

U.S. PATENT DOCUMENTS

| | | | | |
|---|---|---|---|---|
| 6,177,940 B1 * | 1/2001 | Bond | ............. | G06F 19/322 434/262 |
| 6,385,589 B1 * | 5/2002 | Trusheim | ............. | G06F 19/328 705/2 |
| 6,735,569 B1 * | 5/2004 | Wizig | ............. | G06Q 10/1057 705/2 |
| 6,802,810 B2 * | 10/2004 | Ciarniello | ............. | G06Q 40/08 600/300 |
| 7,624,027 B1 * | 11/2009 | Stern | ............. | G06F 19/322 705/2 |
| 7,698,155 B1 * | 4/2010 | Prasad | ............. | G06F 19/328 705/3 |

(Continued)

OTHER PUBLICATIONS

CMS, released Aug. 4, 2011, available online at http://www.calquality.org/storage/documents/resources/2012%20specifications%20for%20medicare%20stars%20measures.pdf.*

(Continued)

*Primary Examiner* — Mark Holcomb
(74) *Attorney, Agent, or Firm* — Stetina Brunda Garred & Brucker

(57) ABSTRACT

Methods and training programs for improving the level of quality of care within a healthcare plan. The methods include obtaining medical data from a population of patients within the plan, storing such data in electronic medical records embodied on a computer readable medium, evaluating at least one metric within the data via a computer capable of interpreting said electronic medical records, and presenting a notification if the metric is found to be below a standard for the metric. The training includes evaluating the healthcare plan's current practices, training the healthcare provider in improved practices, providing a system for recording medical documents, and training the healthcare provider in use of the system.

6 Claims, 1 Drawing Sheet

(56) References Cited

U.S. PATENT DOCUMENTS

| | | | |
|---|---|---|---|
| 7,958,002 B2* | 6/2011 | Bost | 705/7.38 |
| 7,991,626 B2* | 8/2011 | Legorreta et al. | 705/2 |
| 8,078,481 B2* | 12/2011 | Steinbarth | G06Q 40/08 705/4 |
| 8,296,163 B2* | 10/2012 | Fishman | G06F 19/327 600/300 |
| 8,311,854 B1* | 11/2012 | Stanley | G06F 19/322 705/3 |
| 8,521,564 B1* | 8/2013 | Ciechanowski | 705/3 |
| 9,378,531 B2* | 6/2016 | Pecora | G06F 19/36 |
| 2003/0078911 A1* | 4/2003 | Haskell | G06F 19/324 |
| 2004/0078236 A1* | 4/2004 | Stoodley | G16H 10/60 705/2 |
| 2004/0122702 A1* | 6/2004 | Sabol | G06Q 50/22 705/2 |
| 2005/0010440 A1* | 1/2005 | Merkin | G06Q 50/22 705/2 |
| 2006/0281977 A1* | 12/2006 | Soppet | G06F 19/3481 600/300 |
| 2007/0244714 A1* | 10/2007 | McCluskey et al. | 705/2 |
| 2008/0091472 A1* | 4/2008 | Hoppe | G06F 19/327 705/3 |
| 2008/0154642 A1* | 6/2008 | Marble | G16H 15/00 705/3 |
| 2008/0162190 A1* | 7/2008 | Ghouri | G06Q 10/06 705/3 |
| 2009/0055218 A1* | 2/2009 | Ika et al. | 705/2 |
| 2009/0094054 A1* | 4/2009 | Perrin | G06Q 10/0631 705/2 |
| 2009/0113008 A1* | 4/2009 | Gonzalez et al. | 709/206 |
| 2010/0174557 A1* | 7/2010 | Bundschus | G16H 40/20 705/3 |
| 2011/0184759 A1* | 7/2011 | Selker | G06Q 10/10 705/3 |
| 2012/0010900 A1* | 1/2012 | Kaniadakis | G06F 19/328 705/2 |
| 2012/0239430 A1* | 9/2012 | Corfield | G06Q 10/06 705/3 |
| 2012/0303378 A1* | 11/2012 | Lieberman | G06Q 10/10 705/2 |
| 2012/0330681 A1* | 12/2012 | Olalekan | G06Q 50/22 705/3 |

OTHER PUBLICATIONS

Davis, Nancy L., Lloyd Myers, and Zachary E. Myers. "Physician ePortfolio: The missing piece for linking performance with improvement." American Journal of Managed Care 16 (2010): 12. (Year: 2010).*

* cited by examiner

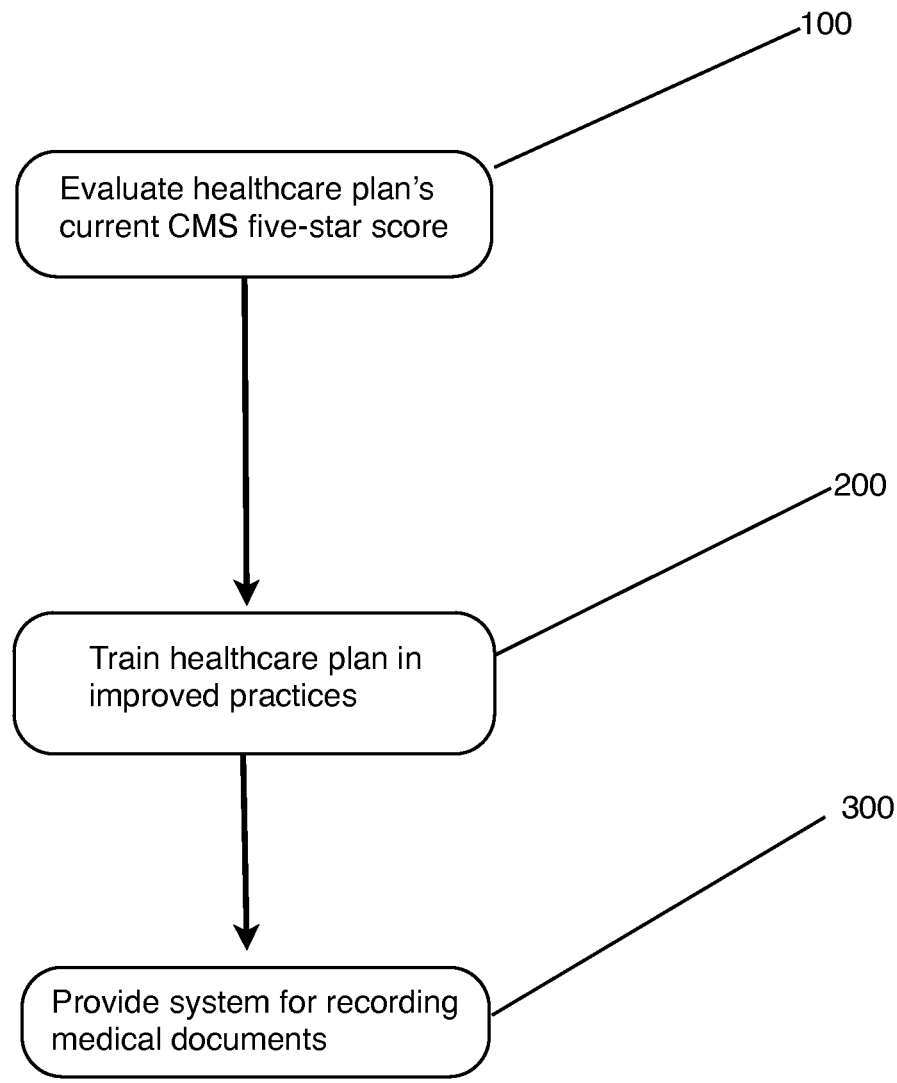

HEALTH PLAN RATING SYSTEM IMPROVEMENT PROGRAM

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention is directed toward improved systems and methods for improving and/or maintaining a high level of performance for healthcare plans. More particularly, the present invention comprises training programs and software systems useful by healthcare plans to improve their Centers for Medicare and Medicaid Services' (CMS) Five-Star Quality Rating.

The Centers for Medicare and Medicaid Services (CMS) rates the relative quality of the private plans that are offered to beneficiaries enrolled in Medicare Advantage programs. CMS rates Medicare Advantage plans on a one to five star scale, with five stars representing the highest quality.

The summary score provides an overall measure of a plan's quality, and is a cumulative indicator of the quality of care, access to care, responsiveness, and beneficiary satisfaction of services provided by the plan.

The ratings are posted on the CMS website to provide beneficiaries with additional information to help them select the best Medicare Advantage plan for them from the plans offered in their service area. The quality rating results are also used by CMS to evaluate a plan's performance and is a method for CMS to reward the high-quality plans for performance excellence. Starting in 2012, the Patient Protection and Affordable Care Act introduces Medicare Advantage bonuses and rebate levels ties to the CMS five-star quality rating. As such, there is a need for healthcare plans to maximize, and maintain, a high quality rating.

CMS defines the star ratings as five stars being excellent performance, four stars being above average performance, three stars being average performance, two stars being below average performance, and one star being poor performance. Healthcare plans receive both a summary score and an overall score. The summary score for Medicare Advantage plans: 1) is used under the health reform law to provide quality-based payments; 2) provides an overall measure of a plan's quality, based on indicators of the quality of care, access to care, responsiveness, beneficiary satisfaction, and customer service; and 3) does not include the plan's Part D (prescription drug plan) ratings. In contrast, the overall score for Medicare Advantage plans differs from the summary score because it combines a plan's summary score with its Part D rating. CMS uses the overall score for the 2011 ratings, and proposes to use the overall score into the future.

The five-star quality scores for Medicare Advantage plans are based on 36 standard performance measures that are derived from four sources: 1) the Healthcare Effectiveness Data and Information Set (HEDIS); 2) the Consumer Assessment of Healthcare Providers and Systems (CAHPS); 3) the Health Outcomes Survey (HOS); and 4) the CMS administrative data, including information about beneficiaries' satisfaction, plans' appeals processes, audit results, and customer service.

Accordingly, there is a need in the art for a program designed to train and support healthcare plans to identify areas of deficiency, thereby finding and driving specific behaviors to improve their star rating and/or to maintain a high star rating.

BRIEF SUMMARY

One aspect of the present invention is directed toward methods of improving the level of quality of care within a healthcare plan. The methods include obtaining medical data from a population of patients within the plan, storing such data in electronic medical records embodied on a computer readable medium, evaluating at least one metric within the data via a computer capable of interpreting said electronic medical records; and presenting a notification if at least one metric is found to be below a standard for the metric. Examples of metrics that may be evaluated include, but are not limited to, whether a disease screening has occurred, whether a vaccination has been administered, and whether a chronic condition is being managed.

Another aspect of the present invention is directed toward methods of training healthcare plans to improve the level of quality of care within the plan. This training includes evaluating the healthcare plan's current practices, training the healthcare provider in improved practices, providing a system for recording medical documents, and training the healthcare provider in use of said system. The system includes a computer readable medium capable of storing medical data obtained from a population of patients, a computer with software capable of evaluating at least one metric of the data stored on the computer readable medium in comparison with a standard for the metric, and a notification system capable of presenting to the user of the system a warning if the metric is found to be below the standard for such metric.

In particular, the training provided may include instructing the healthcare plan to preemptively contact potential at-risk patients.

Yet another aspect of the present invention contemplates a system for recording medical documents. The system includes a computer readable medium capable of storing medical data obtained from a population of patients, a computer with software capable of evaluating at least one metric of the data stored on the computer readable medium in comparison with a standard for the metric, and a notification system capable of presenting to the user of the system a warning if the metric is found to be below the standard for such metric.

For example, the notification system may present a warning if the metric is the percentage of patients within a population receiving a disease screening and the percentage is below a standard assigned for screening the disease, or if patients within a population are determined to be at-risk for medical complications based upon the patients' medical data.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a flowchart depicting the steps for practicing the present invention as it relates to training healthcare plans in improving, or maintaining a high, CMS Star Score.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Referring now to FIG. 1, there is schematically illustrated the various steps by which a method of the present invention operates to train healthcare plans in improving their, or maintaining an already high, CMS Stars Score. In particular, there is a first step 100 of evaluating the healthcare plan's current CMS five-star score. For example, a team consisting of physicians, nurses, and financial auditors may conduct a two day on-site evaluation of the client's current five-star score and activities that determine the client's current score. A written report may be given to the client outlining the team's findings and recommendations that may include staffing requirements, system requirements, and/or a program training and implementation work plan.

The second step 200 includes a comprehensive educational training program. For example, the training program may be offered as a five day class with overhead presentations, case studies, and reference material, with topics including an overview of the Medicare Advantage Part C and Part D Five-Star rating system, improved beneficiary outreach, category and measure details, strategies for improving five-star quality scores, and training on systems for recording medical documents. The training section 200 may include a ninety day post-implementation follow-up with client's staff to evaluate program progress and/or quarterly updates to apprise the client of changes in the CMS Five-Star Quality Rating System.

The third step 300 is providing to the healthcare provider a system for recording medical documents, wherein the system includes at least a computer readable medium capable of storing medical data obtained from patients; a computer with software capable of evaluating the data stored on the computer readable medium; and a notification system capable of compiling the patient medical data and presenting an overall summation of the medical data to the user of the system, thereby indicating steps that may be taken to improve their CMS five-star score. Examples of data to be recorded and information that may be presented by the system are discussed in greater detail below.

In particular, the Affordable Care Act of 2010 mandates that CMS make quality bonus payments (QBPs) to Medicare Advantage (MA) plans that achieve at least four stars in the five-star quality rating system. The star rating scores will be used by CMS to determine if a plan qualifies for bonus payments, as well as being posted on the CMS website to assist beneficiaries in making informed choices when selecting a Medicare Advantage plan. As such, there is a large incentive for healthcare plans to achieve and maintain a high star score.

In order to achieve and maintain a high CMS star score, one must be aware of from where the scores are derived and what steps might be taken to improve the scores. However, for plans offering both Part C and D services, there are total of 9 category areas comprised of 53 individual measures utilized in deriving the score. As such, it can be seen that analyzing and adjusting all of these areas on one's own can be difficult, if not impossible. In particular, for plans covering Part D drug services, the overall score for quality of those services covers 17 different measures in 4 categories: 1) drug plan customer service (including how well the drug plan handles calls and makes decisions about member appeals), 2) drug plan member complaints and Medicare audit findings (including how often members filed a complaint about the drug and findings from Medicare's audit of the plan), 3) member experience with drug plan (including member satisfaction information), and 4) drug pricing and patient safety (including how well the drug plan prices prescriptions and provides updated information on the Medicare website and how often members with certain medical conditions get prescription drugs that are considered safer and clinically recommended for their condition). For Part D coverage, the quality of drug services information comes from the results of Medicare's regular monitoring activities, reviews of billing and other information that plans submit to Medicare, and member surveys conducted by Medicare.

For plans covering Part C health services, the overall score for quality of those services covers 36 different measures in 5 categories: 1) staying healthy as evidenced by screenings, tests, and vaccines (including how often members got various screening tests, vaccines, and other check-ups that help them to stay healthy), 2) managing chronic conditions (including how often members with different conditions got certain tests and treatments that help them to manage their condition), 3) ratings of health plan responsiveness and care (including ratings of member satisfaction with the plan), 4) health plan member complaints and appeals (including how often members filed a complaint against the plan), and 5) health plan telephone customer service (including how well the plan handles calls from members). For Part C coverage, the quality of health services information comes from member surveys administered by Medicare, information from clinics, information submitted by the plans, and results from Medicare's regular monitoring activities.

In particular, for Part C coverage, the measures for each category are shown below in Table 1.

TABLE 1

| Category 1 | Category 2 | Category 3 | Category 4 | Category 5 |
| --- | --- | --- | --- | --- |
| Breast Cancer Screening | Osteoporosis Management in Women Who Have Had a Fracture | Getting Needed Care | Complaints About the Health Plan | Call Center - Hold Time |
| Colorectal Cancer | Diabetes Care - Eye Exam | Doctors Who Communicate | Plan Makes Timely | Call Center - Information |

TABLE 1-continued

| Category 1 | Category 2 | Category 3 | Category 4 | Category 5 |
|---|---|---|---|---|
| Screening | | Well | Decisions About Appeals | Accuracy |
| Cardiovascular Care - Cholesterol Screening | Diabetes Care - Kidney Disease Monitoring | Getting Appointments and Care Quickly | Reviewing Appeals Decisions | Call Center - Foreign Language Interpreter and TTY/TDD Availability |
| Diabetes Care - Cholesterol Screening | Diabetes Care - Blood Sugar Controlled | Customer Service | Corrective Action Plans | |
| Glaucoma Testing | Diabetes Care - Cholesterol Controlled | Overall Rating of Health Care Quality | | |
| Appropriate Monitoring for Patients Taking Long Term Medications | Controlling Blood Pressure | Overall Rating of Plan | | |
| Annual Flu Vaccine | Rheumatoid Arthritis Management | | | |
| Pneumonia Vaccine | Testing to Confirm Chronic Obstructive Pulmonary Disease | | | |
| Improving or Maintaining Physical Health | Improving Bladder Control | | | |
| Improving or Maintaining Mental Health | Reducing the Risk of Falling | | | |
| Osteoporosis Testing | | | | |
| Monitoring Physical Activity | | | | |
| Access to Primary Care Doctor Visits | | | | |

As can be seen from reviewing the contents of Table 1, while there are many factors in determining a plan's five-star score, the bulk of the data is derived from Categories 1 and 2 in relation to staying healthy and managing long-term conditions. Thus, one can more readily improve their score by ensuring these measures are at a high level. For example, the second measure in Category 1, i.e., colorectal cancer screening, is measured based upon the percentage of plan members aged 50-75 who have had the appropriate screening for colorectal cancer. One star is given if less than 36% of these plan members have received the appropriate screening, two stars is given if between 36% and 48% of these plan members have received the appropriate screening, three stars is given if between 48% and 58% of these plan members have received the appropriate screening, four stars is given if between 58% and 70% of these plan members have received the appropriate screening, and five stars is given if 70% or more of these plan members have received the appropriate screening. Similar metrics are utilized for the other measures. However, differing methodologies are utilized for calculating the star rating of various measures, including 1) relative distribution and clustering, 2) relative distribution and significance testing, and 3) a standard, relative distribution, and clustering. Furthermore, these measures, ranges, and methodologies for determining scores are subject to change. Accordingly, it can be seen that it can be exceedingly difficult to predict on one's own what changes to be made within a plan will have a significant change in a plan's overall five-star score. Some of the objects of the present invention are to compile the medical data of plan members, analyze the organized data, and present areas of improvement that will likely result in a higher overall five-star score.

The compilation, organization, analysis, and presentation of data is performed by a software platform (herein referred to as iCode, and additionally disclosed in U.S. patent application Ser. No. 13/167,976, titled Hierarchical Condition Categories Program filed on Jun. 24, 2011, the teachings of which are herein incorporated by reference in their entirety).

iCode allows for the enhanced care of Medicare Advantage enrollees, provides valuable information to the caregiver at the point of care, reduces duplicate and costly services by providing a comprehensive clinical history for each patient, and assists with capturing qualifying HEDIS codes.

In particular, iCode is capable of importing data from a caregiver's current medical records, billing files, health plan claim files, and the like. iCode then auto-populates each field from the data import to create new electronic medical records, analyzes the data, and creates reports of the analyzed data. Examples of such reports include, patient demographic information, health plan eligibility history, outstanding tests/procedures affecting performance per HEDIS measurements, summary of reported chronic conditions, list of potential unreported HEDIS measures, list of three year medical history by ICD-9 and CPT classifications, last six months of pharmacy data, and notes and comments. All captured data fields can be output as an iCode report.

Of particular relevance, however, is the ability of iCode to collect and analyze patient records, and further present to the user areas of deficiency that may be corrected to improve a healthcare plan's five-star score. For example, iCode may warn the user that a particular screening test has not been performed on a sufficient number of patients within a given population (for example an age range or gender), thereby providing an avenue for potential improvement that may raise a plan's five-star score.

Similarly, iCode may identify beneficiaries, based upon disease markers, that may be at-risk and would benefit from increased frequency of visits and intensity of services, enrollment in complex care management, chronic care programs, and/or transitional care programs when appropriate—all designed to ensure the best possible clinical outcome for patients and improved efficiency for healthcare plans. Examples of such other programs are described in U.S. Pat. Nos. 7,657,442 and 7,464,041 and U.S. patent application Ser. No. 11/352,028 and U.S. patent application Ser. No. 12/834,767, the entire teachings of which are collectively incorporated by reference herein. By identifying these potentially at-risk patients, the healthcare plan may preemptively reach out to these beneficiaries thereby more effectively maintaining their health and/or managing their long-term conditions.

Additional modifications and improvements of the present invention may also be apparent to those of ordinary skill in the art. Thus, the particular combinations of parts and steps described and illustrated herein is intended to represent only certain embodiments of the present invention, and is not intended to serve as limitations of alternative devices and methods within the spirit and scope of the invention.

What is claimed is:

1. A method of administering a pneumonia vaccine to improve a quality rating of a healthcare plan, the method comprising:

evaluating a healthcare plan's current practices and current Centers for Medicare and Medicaid Services (CMS) five-star score, the evaluating including conducting a two-day on-site evaluation of the healthcare plan's activities by a team of physicians, nurses, and financial auditors;

providing a written report to the healthcare plan based on the evaluating, the written report outlining the team's findings and recommendations regarding staffing requirements, system requirements, and a program training and implementation work plan;

providing, to one or more healthcare providers associated with the healthcare plan, a system for recording medical documents, the system including a computer readable medium for storing medical data obtained from patients, a computer with software for presenting an overall summation of the stored medical data to a user of the system and evaluating at least one metric of the stored medical data in comparison with a standard for the metric, and a notification system for presenting a warning to the user if the metric is found to be below the standard for the metric;

training the one or more healthcare providers in improved practices, the training including a five day class with overhead presentations, case studies, and reference material regarding topics including an overview of CMS five-star score metrics, improved beneficiary outreach, category and measure details, strategies for improving CMS five-star scores, and training on the system for recording medical documents, the training further including a ninety day post-implementation follow-up to evaluate program progress, the training further including quarterly updates to apprise the healthcare plan of changes in the CMS five-star score metrics;

importing, into the computer, medical records of a plurality of patients enrolled in the healthcare plan along with billing files and health plan claim files of the healthcare plan;

auto-populating each field from the data import to create new electronic medical records;

storing the new electronic medical records in the computer readable medium of the system;

creating and outputting reports of the stored medical records, the reports including patient demographic information, health plan eligibility history, summary of reported chronic conditions, list of three year medical history by International Classification of Diseases (ICD) and Current Procedural Terminology (CPT) classifications, and last six months of pharmacy data;

storing a plurality of CMS five-star score metrics, the CMS five-star score metrics comprising:

category 1 metrics including a breast cancer screening metric, a colorectal cancer screening metric, a cardiovascular care cholesterol screening metric, a diabetes care cholesterol screening metric, a glaucoma testing metric, a long term medications monitoring metric, an annual flu vaccine administration metric, a pneumonia vaccine administration metric, a physical health improvement/maintenance metric, a mental health improvement/maintenance metric, an osteoporosis testing metric, a physical activity monitoring metric, and a primary care doctor visit access metric, and category 2 metrics including an osteoporosis management metric, an eye exam administration metric, a diabetes care kidney disease monitoring metric, a diabetes care blood sugar control metric, a diabetes care cholesterol control metric, a blood pressure control metric, a rheumatoid arthritis management metric, a chronic obstructive pulmonary disease testing metric, a bladder control improvement metric, and a falling risk reduction metric;

periodically updating the stored CMS five-star score metrics;

comparing the stored medical records of the plurality of patients to the stored CMS five-star score metrics to determine one or more areas of deficiency of the healthcare plan that may be corrected to improve a CMS five-star score of the healthcare plan, the comparing including evaluating, for each of the category 1 and category 2 metrics, whether the stored medical records of the plurality of patients indicate that a compliance percentage of the patients, or of an eligible subset plurality thereof, whose medical records show compliance with a screening, test, or vaccine requirement of the metric falls below a threshold percentage specified by the metric, the one or more areas of deficiency of the healthcare plan including a pneumonia vaccine administration deficiency determined on the basis of an evaluation that the stored medical records indicate that a percentage of eligible patients who have been administered the pneumonia vaccine falls below a threshold percentage specified by the pneumonia vaccine administration metric; and, for each of the one or more areas of deficiency of the healthcare plan determined by said comparing:

presenting a computer notification of the area of deficiency using the notification system, the computer notification comprising a warning to the user;

identifying prospective beneficiaries of medical services corresponding to the area of deficiency, the prospective beneficiaries being those patients, from among the plurality of patients, whose stored medical records show non-compliance with the screening, test, or vaccine requirement of the metric corresponding to the area of deficiency and thus contribute to the compliance percentage falling below the threshold percentage specified by the metric; and administering, to the identified prospective beneficiaries, the medical services corresponding to the area of deficiency, wherein, for the pneumonia vaccine administration deficiency of the healthcare plan, the administering includes administering the pneumonia vaccine to the identified prospective beneficiaries.

2. A method of administering a pneumonia vaccine and an annual flu vaccine to improve a quality rating of a healthcare plan, the method comprising:

evaluating a healthcare plan's current practices and current Centers for Medicare and Medicaid Services (CMS) five-star score, the evaluating including conducting a two-day on-site evaluation of the healthcare plan's activities by a team of physicians, nurses, and financial auditors;

providing a written report to the healthcare plan based on the evaluating, the written report outlining the team's findings and recommendations regarding staffing requirements, system requirements, and a program training and implementation work plan;

providing, to one or more healthcare providers associated with the healthcare plan, a system for recording medical documents, the system including a computer readable medium for storing medical data obtained from patients, a computer with software for presenting an overall summation of the stored medical data to a user of the system and evaluating at least one metric of the stored medical data in comparison with a standard for the metric, and a notification system for presenting a warning to the user if the metric is found to be below the standard for the metric;

training the one or more healthcare providers in improved practices, the training including a five day class with overhead presentations, case studies, and reference material regarding topics including an overview of CMS five-star score metrics, improved beneficiary outreach, category and measure details, strategies for improving CMS five-star scores, and training on the system for recording medical documents, the training further including a ninety day post-implementation follow-up to evaluate program progress, the training further including quarterly updates to apprise the healthcare plan of changes in the CMS five-star score metrics;

importing, into the computer, medical records of a plurality of patients enrolled in the healthcare plan along with billing files and health plan claim files of the healthcare plan;

auto-populating each field from the data import to create new electronic medical records;

storing the new electronic medical records in the computer readable medium of the system;

creating and outputting reports of the stored medical records, the reports including patient demographic information, health plan eligibility history, summary of reported chronic conditions, list of three year medical history by International Classification of Diseases (ICD) and Current Procedural Terminology (CPT) classifications, and last six months of pharmacy data;

storing a plurality of CMS five-star score metrics, the CMS five-star score metrics comprising:

category 1 metrics including a breast cancer screening metric, a colorectal cancer screening metric, a cardiovascular care cholesterol screening metric, a diabetes care cholesterol screening metric, a glaucoma testing metric, a long term medications monitoring metric, an annual flu vaccine administration metric, a pneumonia vaccine administration metric, a physical health improvement/maintenance metric, a mental health improvement/maintenance metric, an osteoporosis testing metric, a physical activity monitoring metric, and a primary care doctor visit access metric, and category 2 metrics including an osteoporosis management metric, an eye exam administration metric, a diabetes care kidney disease monitoring metric, a diabetes care blood sugar control metric, a diabetes care cholesterol control metric, a blood pressure control metric, a rheumatoid arthritis management metric, a chronic obstructive pulmonary disease testing metric, a bladder control improvement metric, and a falling risk reduction metric;

periodically updating the stored CMS five-star score metrics;

comparing the stored medical records of the plurality of patients to the stored CMS five-star score metrics to determine one or more areas of deficiency of the healthcare plan that may be corrected to improve a CMS five-star score of the healthcare plan, the comparing including evaluating, for each of the category 1 and category 2 metrics, whether the stored medical records of the plurality of patients indicate a compliance percentage of the patients, or of an eligible subset plurality thereof, whose medical records show compliance with a screening, test, or vaccine requirement of the metric falls below a threshold percentage specified by the metric, the one or more areas of deficiency of the healthcare plan including a pneumonia vaccine administration deficiency determined on the basis of an evaluation that the stored medical records indicate that a percentage of eligible patients who have been administered the pneumonia vaccine falls below a threshold percentage specified by the pneumonia vaccine administration metric, the one or more areas of deficiency of the healthcare plan further including an annual flu vaccine administration deficiency determined on the basis of an evaluation that the stored medical records indicate that a percentage of eligible patients who have been administered the annual flu vaccine falls below a threshold percentage specified by the annual flu vaccine administration metric;

for each of the one or more areas of deficiency of the healthcare plan determined by said comparing, presenting a computer notification of the area of deficiency using the notification system, the computer notification comprising a warning to the user;

for each of the one or more areas of deficiency determined by said comparing, identifying prospective beneficiaries of medical services corresponding to the area of deficiency, the prospective beneficiaries being those patients, from among the plurality of patients, whose stored medical records show non-compliance with the screening, test, or vaccine requirement of the metric corresponding to the area of deficiency and thus contribute to the compliance percentage falling below the threshold percentage specified by the metric; and administering, to the identified prospective beneficiaries associated with each of the one or more areas of deficiency of the healthcare plan, the medical services corresponding to the area of deficiency, wherein the administering includes administering the pneumonia vaccine and the annual flu vaccine to a patient who is both one of the prospective beneficiaries identified for the pneumonia vaccine administration deficiency and one of the prospective beneficiaries identified for the annual flu vaccine administration deficiency.

3. A method of screening for colorectal cancer to improve a quality rating of a healthcare plan, the method comprising:

evaluating a healthcare plan's current practices and current Centers for Medicare and Medicaid Services (CMS) five-star score, the evaluating including conducting a two-day on-site evaluation of the healthcare plan's activities by a team of physicians, nurses, and financial auditors;

providing a written report to the healthcare plan based on the evaluating, the written report outlining the team's findings and recommendations regarding staffing requirements, system requirements, and a program training and implementation work plan;

providing, to one or more healthcare providers associated with the healthcare plan, a system for recording medical documents, the system including a computer readable medium for storing medical data obtained from patients, a computer with software for presenting an overall summation of the stored medical data to a user of the system and evaluating at least one metric of the stored medical data in comparison with a standard for the metric, and a notification system for presenting a warning to the user if the metric is found to be below the standard for the metric;

training the one or more healthcare providers in improved practices, the training including a five day class with overhead presentations, case studies, and reference material regarding topics including an overview of CMS five-star score metrics, improved beneficiary outreach, category and measure details, strategies for improving CMS five-star scores, and training on the system for recording medical documents, the training further including a ninety day post-implementation follow-up to evaluate program progress, the training further including quarterly updates to apprise the healthcare plan of changes in the CMS five-star score metrics;

importing, into the computer, medical records of a plurality of patients enrolled in the healthcare plan along with billing files and health plan claim files of the healthcare plan;

auto-populating each field from the data import to create new electronic medical records;

storing the new electronic medical records in the computer readable medium of the system;

creating and outputting reports of the stored medical records, the reports including patient demographic information, health plan eligibility history, summary of reported chronic conditions, list of three year medical history by International Classification of Diseases (ICD) and Current Procedural Terminology (CPT) classifications, and last six months of pharmacy data;

storing a plurality of CMS five-star score metrics, the CMS five-star score metrics comprising:

category 1 metrics including a breast cancer screening metric, a colorectal cancer screening metric, a cardiovascular care cholesterol screening metric, a diabetes care cholesterol screening metric, a glaucoma testing metric, a long term medications monitoring metric, an annual flu vaccine administration metric, a pneumonia vaccine administration metric, a physical health improvement/maintenance metric, a mental health improvement/maintenance metric, an osteoporosis testing metric, a physical activity monitoring metric, and a primary care doctor visit access metric, and category 2 metrics including an osteoporosis management metric, an eye exam administration metric, a diabetes care kidney disease monitoring metric, a diabetes care blood sugar control metric, a diabetes care cholesterol control metric, a blood pressure control metric, a rheumatoid arthritis management metric, a chronic obstructive pulmonary disease testing metric, a bladder control improvement metric, and a falling risk reduction metric;

periodically updating the stored CMS five-star score metrics;

comparing the stored medical records of the plurality of patients to the stored CMS five-star score metrics to determine one or more areas of deficiency of the healthcare plan that may be corrected to improve a CMS five-star score of the healthcare plan, the comparing including evaluating, for each of the category 1 and category 2 metrics, whether the stored medical records of the plurality of patients indicate that a compliance percentage of the patients, or of an eligible subset plurality thereof, whose medical records show compliance with a screening, test, or vaccine requirement of the metric falls below a threshold percentage specified by the metric, the one or more areas of deficiency of the healthcare plan including a colorectal cancer screening deficiency determined on the basis of an evaluation that the stored medical records indicate that a percentage of eligible patients who have been screened for colorectal cancer falls below a threshold percentage specified by the colorectal cancer screening metric; and, for each of the one or more areas of deficiency of the healthcare plan determined by said comparing:

presenting a computer notification of the area of deficiency using the notification system, the computer notification comprising a warning to the user;

identifying prospective beneficiaries of medical services corresponding to the area of deficiency, the prospective beneficiaries being those patients, from among the plurality of patients, whose stored medical records show non-compliance with the screening, test, or vaccine requirement of the metric corresponding to the area of deficiency and thus contribute to the compliance percentage falling below the threshold percentage specified by the metric; and administering, to the identified prospective beneficiaries, the medical services corresponding to the area of deficiency, wherein, for the colorectal cancer screening deficiency of the healthcare plan, the administering includes screening the identified prospective beneficiaries for colorectal cancer.

4. The method of claim 3, wherein the colorectal cancer screening deficiency of the healthcare plan is determined on the basis of an evaluation that the stored medical records indicate that a percentage of the patients aged 50-75 who have been screened for colorectal cancer falls below a threshold percentage specified by the colorectal cancer screening metric.

5. The method of claim 4, wherein the threshold percentage specified by the colorectal cancer screening metric is 70%.

6. The method of claim 4, wherein the threshold percentage specified by the colorectal cancer screening metric is 58%.

\* \* \* \* \*